(12) United States Patent
Newton et al.

(10) Patent No.: US 11,013,862 B2
(45) Date of Patent: May 25, 2021

(54) CARTRIDGE RETAINER FOR AN INJECTION DEVICE

(71) Applicant: Antares Pharma, Inc., Ewing, NJ (US)

(72) Inventors: Benjamin Newton, Chanhassen, MN (US); Steven Andreas Anderson, Shakopee, MN (US)

(73) Assignee: Antares Pharma, Inc., Ewing, NJ (US)

(*) Notice: Subject to any disclaimer, the term of this patent is extended or adjusted under 35 U.S.C. 154(b) by 98 days.

(21) Appl. No.: 16/381,374

(22) Filed: Apr. 11, 2019

(65) Prior Publication Data

US 2019/0231980 A1    Aug. 1, 2019

Related U.S. Application Data

(63) Continuation of application No. 15/516,170, filed as application No. PCT/US2015/057042 on Oct. 23, 2015, now Pat. No. 10,265,475.

(60) Provisional application No. 62/067,488, filed on Oct. 23, 2014.

(51) Int. Cl.
*A61M 5/24* (2006.01)
*A61M 5/34* (2006.01)

(52) U.S. Cl.
CPC .......... *A61M 5/2466* (2013.01); *A61M 5/24* (2013.01); *A61M 5/347* (2013.01); *A61M 2005/244* (2013.01); *A61M 2005/2474* (2013.01); *A61M 2205/0216* (2013.01)

(58) Field of Classification Search
CPC .... A61M 5/24; A61M 5/2033; A61M 5/3202; A61M 5/3204; A61M 5/2466; A61M 5/3271; A61M 5/20; A61M 5/3243; A61J 1/2096
See application file for complete search history.

(56) References Cited

U.S. PATENT DOCUMENTS

| | | | |
|---|---|---|---|
| 3,976,069 A | 8/1976 | Ong | |
| 4,031,893 A | 6/1977 | Kaplan et al. | |
| 5,078,398 A | 7/1992 | Stiehl et al. | |
| 6,585,702 B1* | 7/2003 | Brunel | A61M 5/3202 604/263 |
| 6,872,194 B2 | 3/2005 | Doyle et al. | |
| 7,004,929 B2 | 2/2006 | McWethy et al. | |
| 2002/0151849 A1* | 10/2002 | West | A61M 5/34 604/181 |

FOREIGN PATENT DOCUMENTS

WO    2014/165142 A1    10/2014

OTHER PUBLICATIONS

International Search Report and Written Opinion dated Jan. 11, 2016 for International Application No. PCT/ US2015/057042.

* cited by examiner

*Primary Examiner* — Manuel A Mendez
(74) *Attorney, Agent, or Firm* — Morgan, Lewis & Bockius LLP

(57) ABSTRACT

A cartridge retainer comprises a sleeve having a distal end a proximal end and a longitudinal axis extending between the distal end and the proximal end. One or more tabs extend radially from the sleeve toward the longitudinal axis and are configured to radially deflect away from the longitudinal axis. One or more deformable members extend axially from the distal end of the sleeve toward the one or more tabs and are configured to deform in a longitudinal direction toward the distal end.

20 Claims, 7 Drawing Sheets

CARTRIDGE RETAINER FOR AN INJECTION DEVICE

CROSS-REFERENCE TO RELATED APPLICATIONS

This application is a continuation of U.S. patent application Ser. No. 15/516,170 filed Mar. 31, 2017, which is a U.S. National Stage filing of International Patent Application No. PCT/US2015/057042 filed Oct. 23, 2015, which claims the benefit of U.S. Provisional Patent Application No. 62/067,488 filed Oct. 23, 2014 entitled "Cartridge Retainer For An Injection Device", each of which is incorporated by reference herein in its entirety.

FIELD OF THE INVENTION

The present invention generally relates to cartridge retainer and, more particularly, to a cartridge retainer for use in an injection device.

BRIEF SUMMARY OF THE INVENTION

In one embodiment there is a cartridge retainer comprising: a sleeve having a distal end, a proximal end and a longitudinal axis extending between the distal end and the proximal end; one or more tabs extending radially from the sleeve toward the longitudinal axis and configured to radially deflect away from the longitudinal axis; and one or more deformable members extending axially from the distal end of the sleeve toward the one or more tabs and configured to deform in a longitudinal direction toward the distal end. In one embodiment, the one or more deformable members include at least one projection. In one embodiment, the at least one projection is a radially extending and axially projecting rib having a taper in the longitudinal direction. In one embodiment, the at least one projection includes a plurality of projections spaced equally from one another around the longitudinal axis.

In one embodiment, the one or more deformable members is configured to deform such that a space between the one or more deformable members and the one or more tabs is variable. In one embodiment, the one or more tabs are configured to radially deflect away from the longitudinal axis during insertion of a cap of a cartridge and at least partially return to an initial position to abut a bottom surface of the cap in an inserted position, and wherein the one or more deformable members are configured to abut a top surface of the cap and axially deform during insertion of the cartridge such that the cap is sandwiched between the one or more deformable members and the one or more tabs in the inserted position. In one embodiment, the one or more tabs include a cantilever projection extending toward the distal end of the sleeve. In one embodiment, the one or more tabs are substantially rigid in a longitudinal direction toward the proximal end of the sleeve.

In one embodiment, the one or more deformable members includes an elastomeric material. In one embodiment, the one or more deformable members is an o-ring. In one embodiment, the one or more deformable members is a spring. In one embodiment, the one or more deformable members and the sleeve are comprised of the same material and are integrally formed. In a further embodiment, the cartridge retainer further comprises a cartridge having a cap, wherein the cap is sandwiched between the one or more deformable members and the one or more tabs in an inserted position.

In another embodiment there is a cartridge retainer comprising: a sleeve having a distal end, a proximal end and a longitudinal axis extending between the distal end and the proximal end; a plurality of cantilever tabs extending from an inner surface of the sleeve toward the distal end of the sleeve and the longitudinal axis and configured to radially deflect away from the longitudinal axis, the plurality of tabs being substantially rigid in a longitudinal direction toward the proximal end of the sleeve; and one or more projections integrally formed with the sleeve and extending axially from the distal end of the sleeve toward the one or more tabs and configured to deform in a longitudinal direction toward the distal end of the sleeve.

In another embodiment there is a cartridge retainer comprising: a sleeve having a distal end, a proximal end and a longitudinal axis extending between the distal end and the proximal end; and at least one contact member projecting radially inwardly from the sleeve toward the longitudinal axis, the at least one contact member configured to radially deform radially away from the longitudinal axis, the at least one contact member being comprised of an elastomeric material. In one embodiment, the at least one contact member includes at least three ribs that are each generally parallel with the longitudinal axis. In one embodiment, the at least three ribs are coupled to one another by a ring comprised of an elastomeric material.

BRIEF DESCRIPTION OF THE SEVERAL VIEWS OF THE DRAWINGS

The following detailed description of embodiments of the cartridge retainer will be better understood when read in conjunction with the appended drawings of an exemplary embodiment. It should be understood, however, that the invention is not limited to the precise arrangements and instrumentalities shown.

In the drawings.

DETAILED DESCRIPTION OF THE INVENTION

Figure 1:
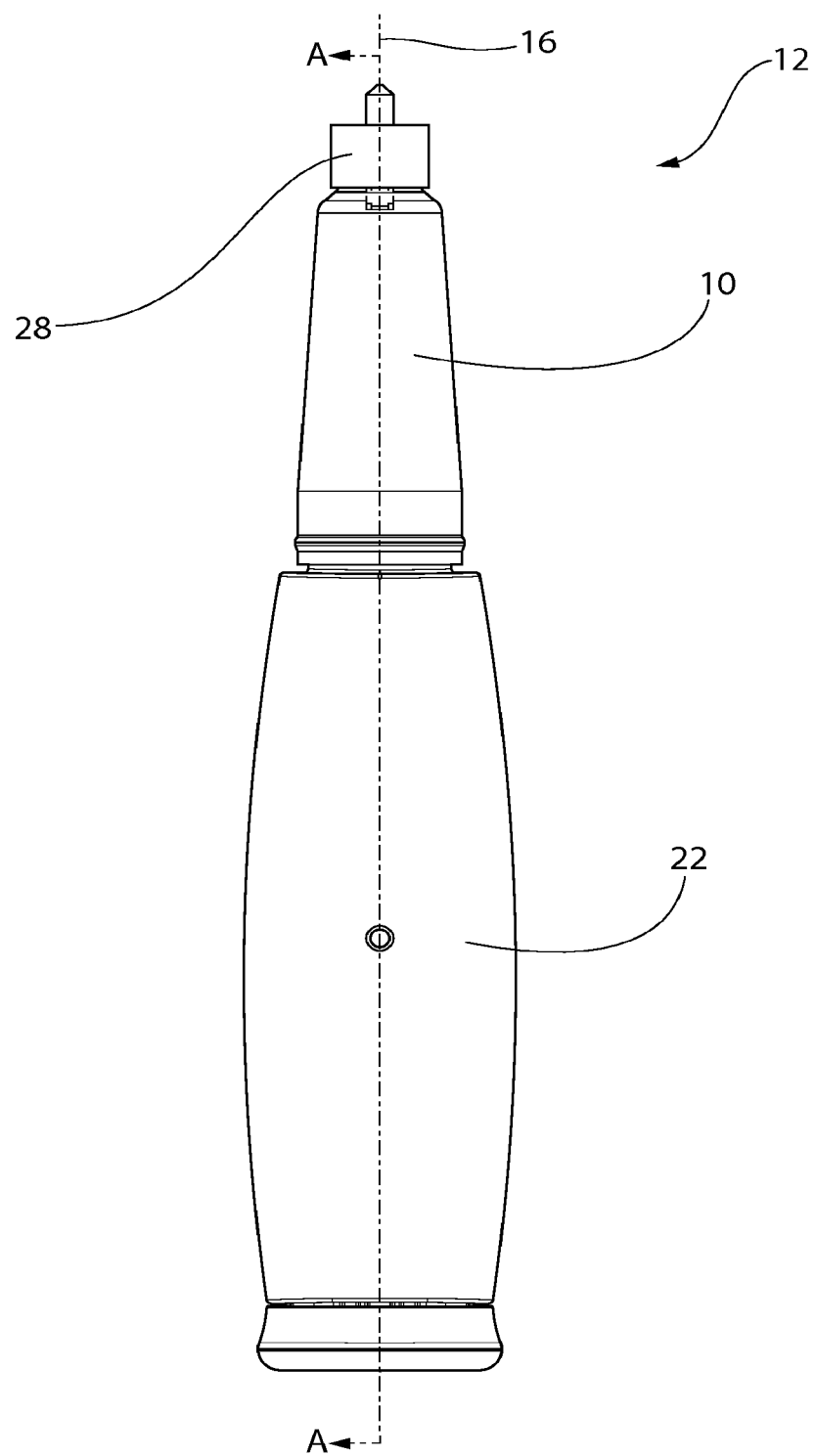
FIG. 1 is a side view of an injection device having a cartridge retainer in accordance with an exemplary embodiment of the present invention.

Referring to the drawings in detail, wherein like reference numerals indicate like elements throughout, there is shown in FIGS. 1-5A a cartridge retainer, generally designated 10, in accordance with an exemplary embodiment of the present invention. The cartridge retainer 10 is configured to be used with an injection device 12.

Figure 2:
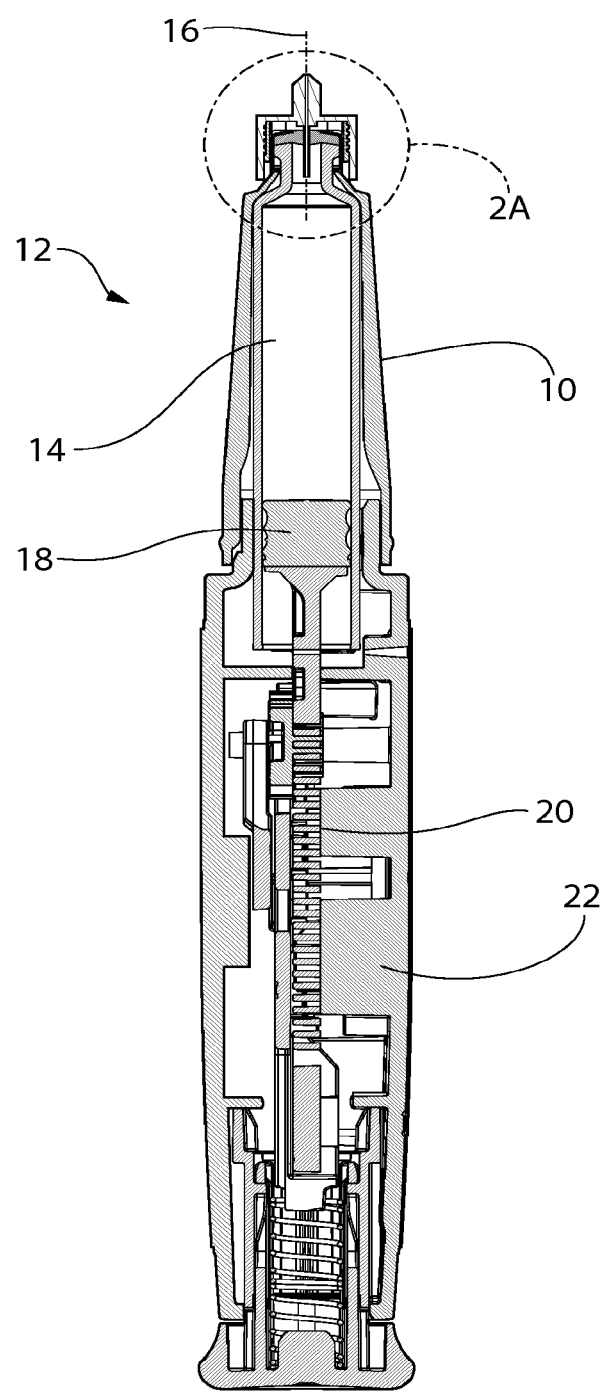
FIG. 2 is a cross sectional view of the injection device shown in FIG. 1 taken along a plane indicated by line A-A.
Figure 2A:
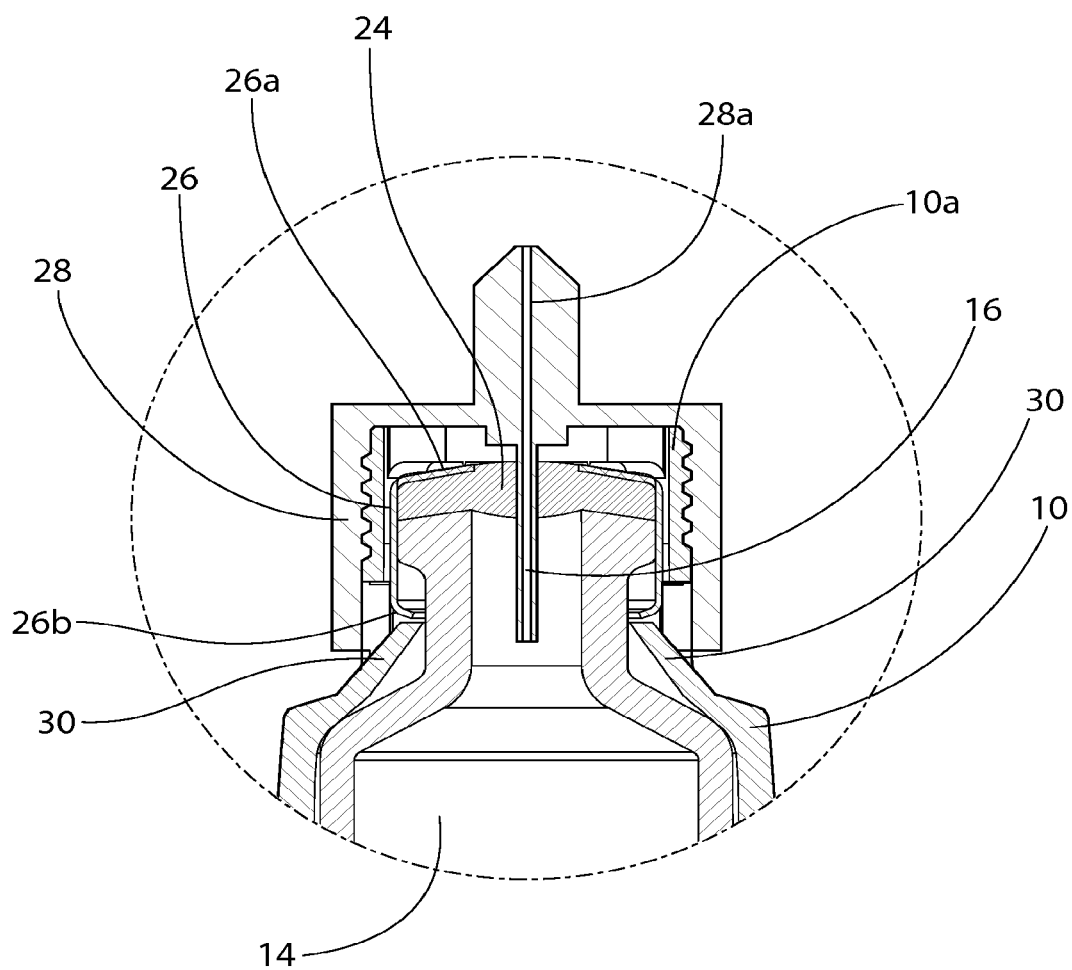
FIG. 2A is an enlarged view of the injection device shown in FIG. 2 within circle 2A.

Referring to FIGS. 1-2A, injection devices 12, such as pen injectors, contain a cartridge 14 that contains a fluid to be injected into a user through a needle 16. The cartridge retainer 10 is configured to house and retain the cartridge 14. The cartridge 14 may be sealed at a proximal end by a slideable piston 18. The injection device 12 may include an actuator 20 within a housing 22 configured to act on the piston 18 and urge the piston 18 through the cartridge 14 to deliver the fluid to the patient through the needle 16. The cartridge retainer 10 may be removeably attached to the housing 22. In one embodiment, the cartridge retainer 10 is threadably coupled with the housing 22. The cartridge retainer 10 may be used with any injection device including those disclosed in international patent application publication No. WO 2014/164786 which is hereby incorporated by reference in its entirety.

Referring to FIG. 2A, the cartridge 14 may include a septum 24 that seals the distal end of the cartridge 14. The septum 24 may be configured to be pierced by the needle 16. The septum 24 may be comprised of an elastomeric material that reseals the cartridge 14 upon removeable of the needle 16 from the septum 24. The septum 24 may be secured to the cartridge 14 by a cap 26. In one embodiment, the cap 26 is comprised of a metal such as aluminum that is crimped onto the distal tip of the cartridge 14 to pinch the septum 24 onto the cartridge 14. The cap 26 may include a top surface 26a and a bottom surface 26b. The top surface 26a and the bottom surface 26b may face in generally opposite directions.

The needle 16 may be coupled to a hub 28. In one embodiment, the needle 16 includes two needles extending from opposite ends of a fluid passageway 28a. In other embodiments, the needle 16 is a single needle 16 that extends from both ends of the hub 28. The hub 28 may be releaseably attached to the distal end 10a of the cartridge retainer 10. In one embodiment, the hub 28 is threadably attached to the distal end 10a of the cartridge retainer 10. In one embodiment, attaching the hub 28 to the cartridge retainer 10 causes the needle 16 to pierce the septum 24.

In some embodiments, the cartridge 14 is configured to be used for multiple injections. In some embodiments, a new double hub needle 16 is attached to the injection device 12 prior to each injection. In other embodiments, the cartridge 14 is configured to be used in a single use injection device.

Holding the cartridge 14 in place relative to the injection device 12 may be more desirable than in the past to assure that the correct dosage is delivered to the patient. The variability in the dimensions of the glass of the cartridge 14, the variability of the thickness and durometer of the septum 24, and changes in International Organization for Standardization (ISO) specifications of various components such as a thicker and tougher septum, among other things, may result in difficulty in retaining the cartridge in place relative to the cartridge retainer 10 to the desired amount. The desire to deliver smaller and more accurate dosages and the cost of the drug may further increase the need to hold the cartridge 14 in place and may render previously acceptable retention mechanisms unacceptable.

Referring to FIGS. 2 and 2A, as a user presses the needle 16 through the septum 24, the force of the needle insertion is carried through the cartridge 14. If the cartridge 14 is unsupported in relation to the cartridge sleeve 10, this needle insertion force is transmitted directly to the actuator 20 which in turn compresses the piston 18 within the cartridge 14. As the needle 16 pierces the septum 24, the piston 18 may spring back and thus eject fluid out of the needle 16.

In one embodiment, the following equation calculates the amount of slop or movement between the cartridge 14 and cartridge retainer 10 that could result in 0.010 mL of fluid loss due to needle insertion: $\Pi * R^2 * H = V$, where: $R = 4.85$ mm (nominal inside radius of a 3.0 mL cartridge), H=height of a volumetric disc, V=0.010 mL (one side of the typical ±0.010 nit tolerance band, assumed fluid density of 1.00). Solving for H: H=0.135 mm, or 0.005". Thus, if the cartridge 14 slips 0.005" in relation to the cartridge retainer 10 during needle insertion, 0.010 mL of fluid could be ejected from the cartridge 14. In one embodiment, the cartridge retainer 10 retains the cartridge 14 such that the cartridge 14 moves less than 0.005 in the longitudinal direction relative to the cartridge retainer 10.

In one embodiment, a portion of the cartridge 14 is secured relative to the cartridge retainer 10 by at least two axially opposed features. In one embodiment, one of these features is deformable allowing for variability in the size of the portion of the cartridge 14 being retained. In one embodiment, the cartridge 14 is secured relative to the cartridge retainer 10 by retaining the cap 26 of the cartridge 14. In one embodiment, the cartridge 14 is retained in the cartridge retainer 10 such that attaching the needle 16 to the cartridge 14 does not move the cartridge 14 and no priming of the injection device 12 is required even on the first injection.

Figure 4:
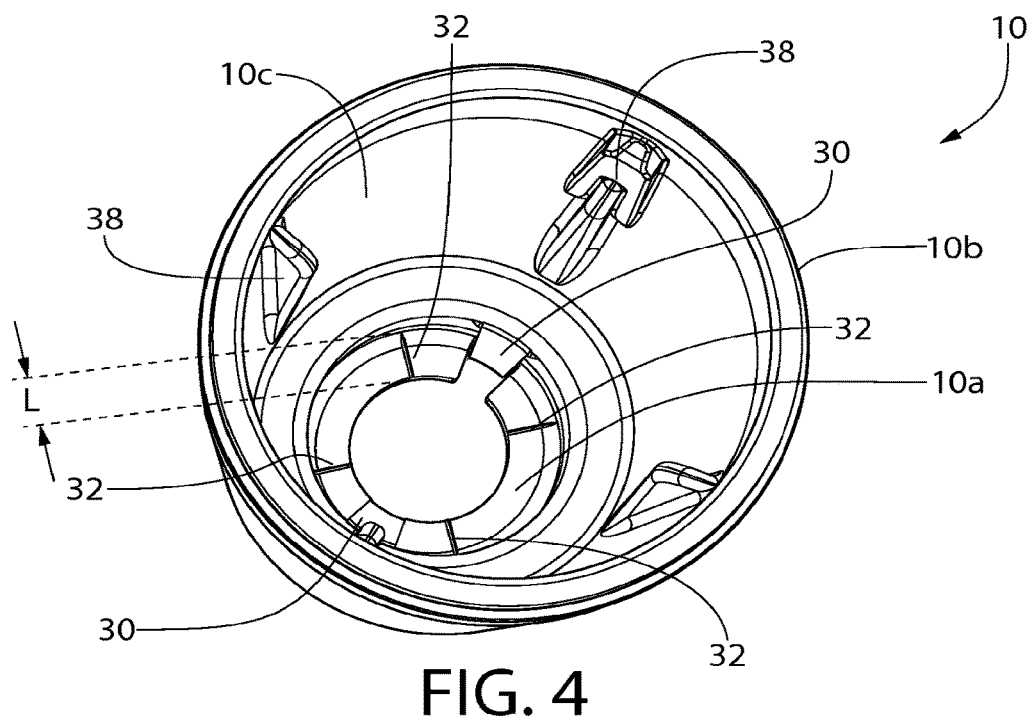
FIG. 4 is a bottom perspective view of the cartridge retainer shown in FIG. 1.
Figure 5:
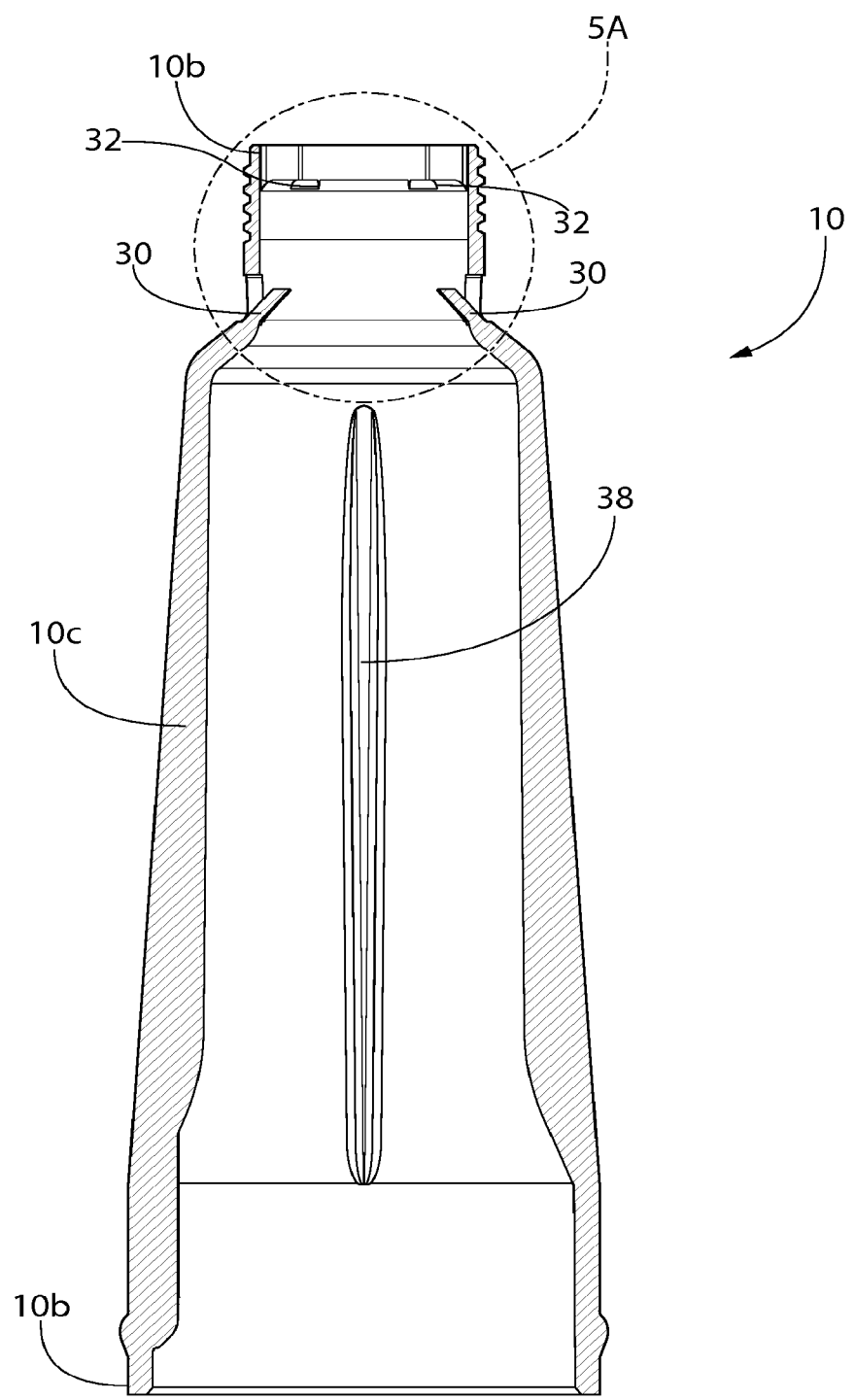
FIG. 5 is a cross sectional view of the cartridge retainer shown in FIG. 1 taken along a plane indicated by line A-A.
Figure 5A:
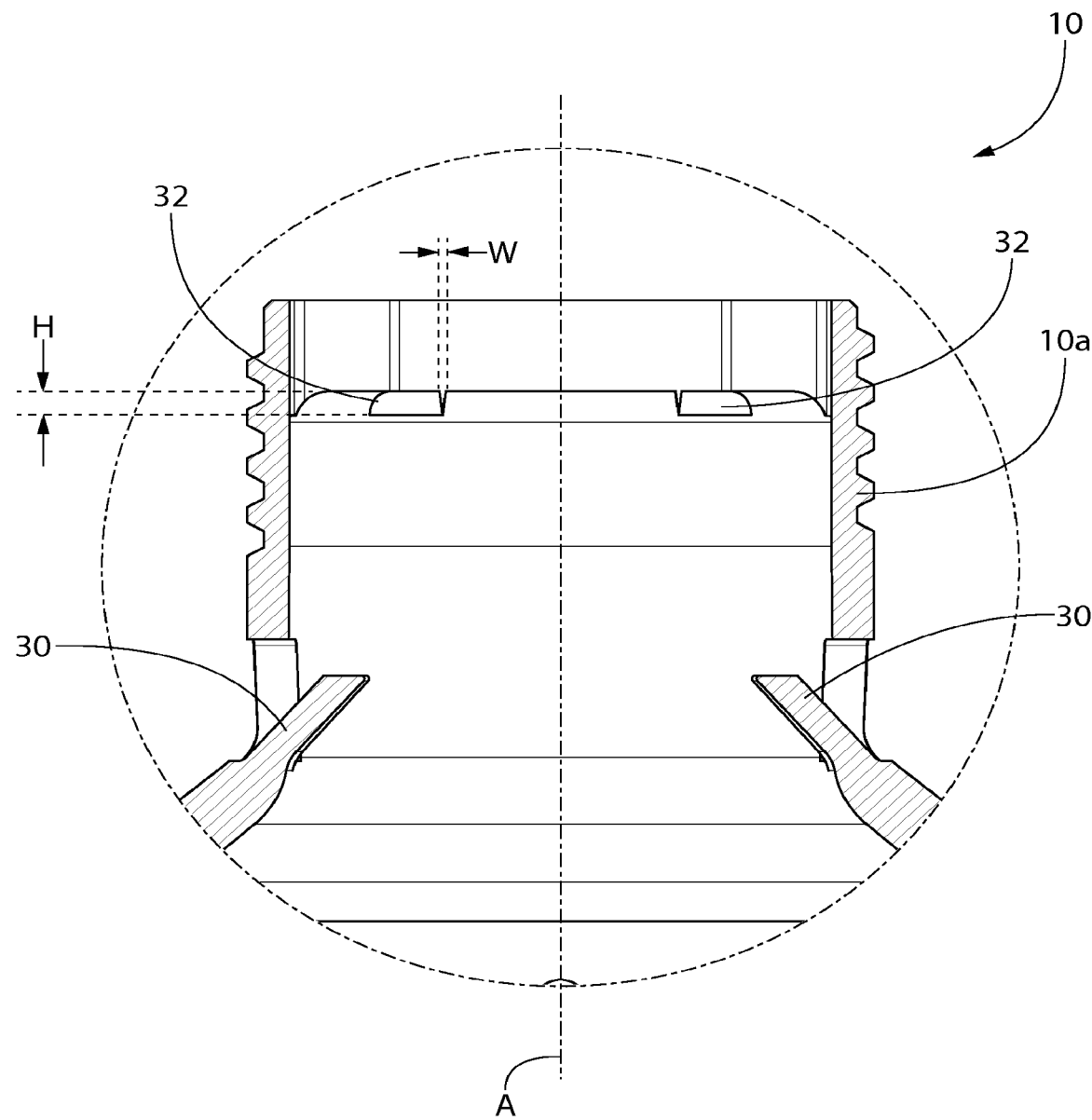
FIG. 5A is an enlarged view of the cartridge retainer shown in FIG. 5 within circle 5A.

Referring to FIGS. 4, 5 and 5A, the cartridge retainer 10 includes one or more features configured to sufficiently retain the cartridge 14 in place relative to the remainder of the injection device 12 during use. The cartridge retainer 10 may include one or more tabs 30 and/or one or more deformable members 32 configured to retain the cartridge 14 in place relative to the cartridge retainer 10.

Figure 3:
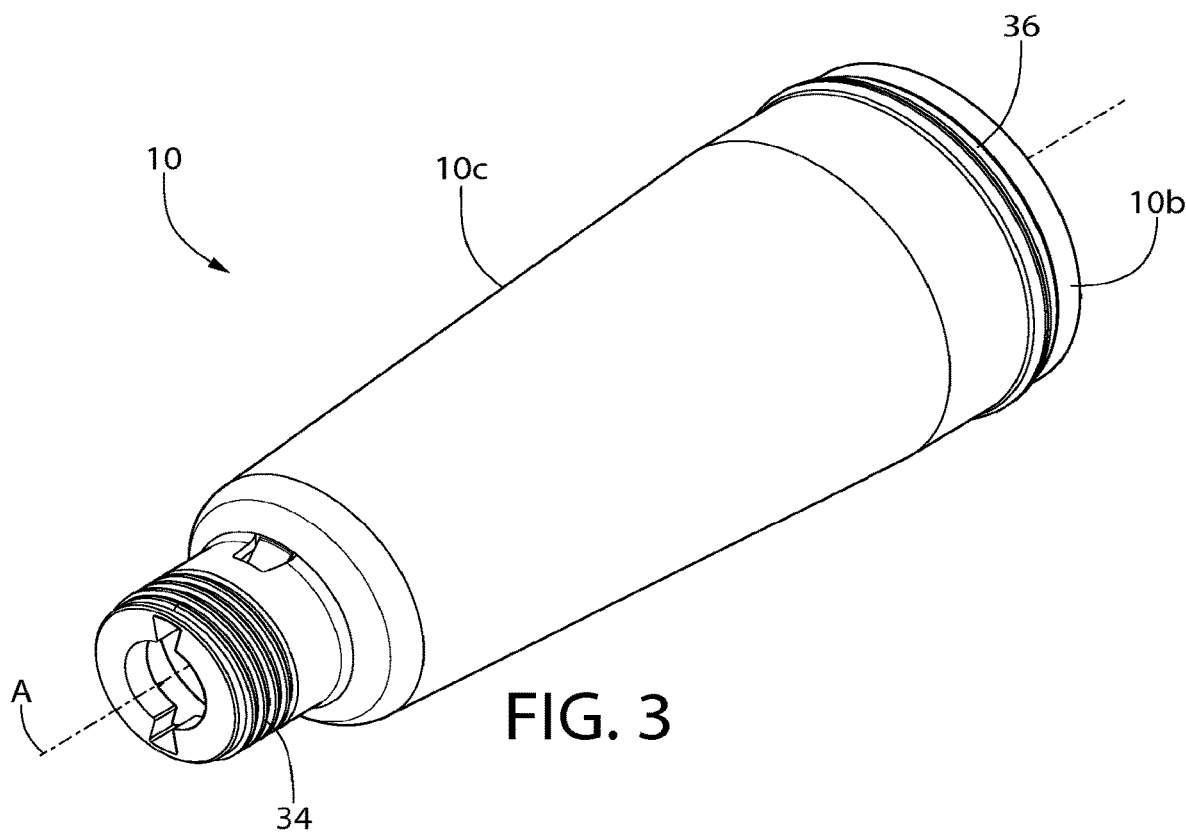
FIG. 3 is a side perspective view of the cartridge retainer shown in FIG. 1.

Referring to FIG. 3, the cartridge retainer 10 may include a sleeve 10c having a distal end 10a a proximal end 10b and a longitudinal axis A extending between the distal end 10a and the proximal end 10b. The sleeve 10c may extend entirely around the longitudinal axis A to form a solid sidewall. In other embodiments, the sleeve 10c includes one or more apertures or windows. In one embodiment, the sleeve 10c tapers toward the distal end 10a. The distal end 10a may include threads 34 configured to engage corresponding threads of the hub 28 of the needle 16 (see FIG. 2A). The proximal end 10b may include threads 36 configured to engage corresponding threads of the housing 22 (see FIG. 2). In other embodiments, the cartridge retainer 10 may be coupled to the needle 16 and the housing 22 by other configurations such as snap fit or one or more fasteners.

Referring to FIGS. 4 and 5A, the one or more tabs 30 may extend radially from the sleeve 10c toward the longitudinal axis A and configured to radially deflect away from the longitudinal axis A while inserting cap 26 into the distal end 10a of the cartridge retainer 10. The one or more tabs 30 may be configured to radially deflect away from the longitudinal axis A during insertion of the cap 26 and at least partially return to an initial position to abut the bottom surface 26b of the cap 26 in an inserted position (see FIG. 2A). The one or more tabs 30 may include a cantilever projection extending toward the distal end 10a of the cartridge retainer 10. In one embodiment, the one or more deformable members 32 exert a force against the top surface 26a of the cap to retain the bottom surface 26b of the cap 26 against the one or more tabs 30 (see FIG. 2A). The one or more tabs 30 may be substantially rigid in a longitudinal direction toward the proximal end 10b of the cartridge retainer 10 such that the one or more tabs 30 prevent the cartridge 14 from being pulled back out from the cartridge retainer 10 after insertion. In one embodiment, the one or more tabs 30 include two diametrically opposed tabs. In other embodiments, three or more tabs 30 are provided that may be equally or unequally spaced around the longitudinal axis A.

Referring to FIGS. 2, 4 and 5A, the one or more deformable members 32 may be provided, to allow for caps 26 (see FIG. 2A) of various heights in the longitudinal direction to be inserted between the one or more tabs 30 and the one or more deformable members 32. The one or more deformable members 32 may be configured to contact the top surface 26a of the cap 26 before the bottom surface 26b clears the one or more tabs 30 in the longitudinal direction. As the cap 26 clears the one or more tabs 30 in the longitudinal direction, the top surface 26a abuts and axially deforms the one or more deformable members 32 such that the cap 26 is sandwiched between the one or more deformable members 32 and the one or more tabs 30 in the inserted position.

Referring to FIGS. 4 and 5A, the one or more deformable members 32, also referred to as crush features or crush ribs, may be integrally formed with the sleeve 10c. The one or more deformable members 32 may be crushed or flattened as the cap 26 is inserted. In one embodiment, the one or more deformable members 32 plastically deform upon contact with the cap 26. In other embodiments, the one or more deformable members 32 plastically and elastically deform upon contact with the cap 26. In other embodiments, the one or more deformable members 32 fully elastically deform upon contact with the cap 26. In one embodiment, the one or more deformable members 32 are comprised of the same material as the sleeve 10c. In one embodiment, the one or more deformable members 32 are comprised of a polycarbonate. In other embodiments, the one or more deformable members 32 include an elastomeric material. In one embodiment, the one or more deformable members 32 include an elastomeric o-ring. In one embodiment, the one or more deformable members 32 include a spring.

The one or more deformable members 32 may extend axially from the distal end 10a of the sleeve 10c toward the one or more tabs 30 and are configured to deform in a longitudinal direction toward the distal end 10a. The one or more deformable members 32 may include at least one projection. The at least one projection may be a radially extending and axially projecting rib having a taper in the longitudinal direction. In one embodiment, the one or more deformable members 32 have a length L of approximately 0.060 inches (see FIG. 4) a height H of approximately 0.010 inches to approximately 0.020 inches and a width at the base of approximately 0.005 inches to approximately 0.015 inches (see FIG. 5A). In one embodiment, the one or more deformable members 32 deform in the longitudinal direction approximately 0.005 inches to approximately 0.010 inches. In one embodiment, the one or more deformable members 32 include four ribs spaced equally around the longitudinal axis A. In other embodiments, three or more deformable members 32 are provided that may be equally or unequally spaced around the longitudinal axis A. In one embodiment, the one or more deformable members 32 have a triangular cross section. In other embodiments, the one or more deformable members 32 have another cross sectional shape such as rectangular or parabolic or a different shape such as conic. The one or more deformable members 32 may be the same size and shape as the other deformable members 32 or they may be sized and/or shaped differently from one another.

Referring to FIGS. 4 and 5, the sleeve 10c may include one or more radially projecting and longitudinally extending ribs 38 configured to engage the outer sidewall of the cartridge 14. The ribs 38 may be tapered such that the cartridge 14 is snugly radially secured in the cartridge retainer 10 in the inserted position. In one embodiment, the ribs 38 include four ribs spaced equally around the longitudinal axis A. In one embodiment, the ribs 38 include one or more deformable members similar to deformable members 32 to accommodate cartridges 14 having diameters of varying size.

Figure 6:
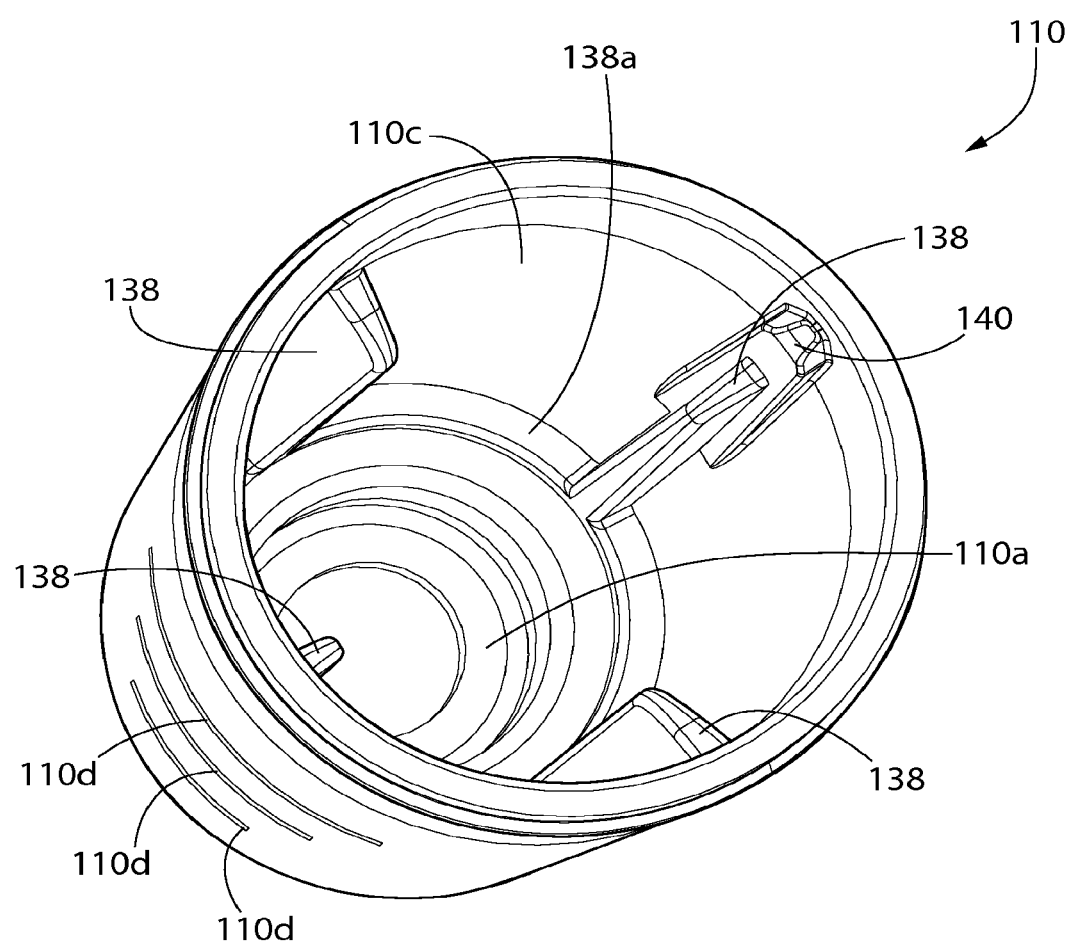
FIG. 6 is a bottom perspective view of a cartridge retainer in accordance with another exemplary embodiment of the present invention.

Referring to FIG. 6, another exemplary embodiment of the cartridge retainer, generally designated 110, is shown. The sleeve 110c of the cartridge retainer 110 may include one or more elastomeric contact members configured to engage the outer sidewall of the cartridge 14 (see FIG. 2). The elastomeric contact members may include one or more radially projecting and longitudinally extending ribs 138. The ribs 138 may be generally parallel with the longitudinal axis A (see FIG. 3). The ribs 138 may be tapered radially inwardly toward the distal end 110a such that the cartridge 14 is snugly secured in the cartridge retainer 110 in the inserted position. In one embodiment, the ribs 138 include four ribs spaced equally around the longitudinal axis A. In one embodiment, the ribs 138 include four ribs spaced around the longitudinal axis A. In one embodiment, the ribs 138 include at least three ribs spaced around the longitudinal axis A. In one embodiment, the ribs 138 include three ribs spaced equally around the longitudinal axis A. In one embodiment, the ribs 138 include at least two ribs spaced around the longitudinal axis A. In one embodiment, the ribs 138 include two ribs diametrically spaced from one another.

The ribs 138 may be comprised of a different material than the sleeve 110c. The ribs 138 may be comprised of a material that is more flexible than the sleeve 110c to accommodate cartridges 14 having diameters of varying size. In one embodiment, the ribs 138 are comprised of an elastomeric material. In one embodiment, the ribs 138 are comprised of urethane. In one embodiment, the ribs 138 are comprised of a thermoplastic elastomer having a low modulus.

The ribs 138 may be coupled together by one or more cross members 138a. The one or more cross members 138a may include a ring extending circumferentially around the longitudinal axis A on the inner sidewall of the sleeve 110c and positioned toward the distal end 110a. The cross members 138a may couple the ribs 138 to one another. In one embodiment, the cross members 138a extend along the inner wall of sleeve 110c independent of and in the absence of ribs 138. The ring 138a may be integral with and comprised of the same material as the ribs 138. In one embodiment, the ring 138a is sized and positioned to contact the outer sidewall of the cartridge 14. The ribs 138 and ring 138a may be co-molded or two shot injection molded with the sleeve 110c. In one embodiment, the ribs 138 and the ring 138a are glued to the sleeve 110c.

The cartridge retainer 110 may include one or more keys 140 to help align and couple with a corresponding key of the housing 22 (see FIG. 2). In one embodiment, the key 140 is a radial projection that projects inwardly and extending longitudinally. In one embodiment, the key 140 is positioned between a rib 138 and the inner sidewall of the sleeve 110c.

The sleeve 110c may include one or more windows 110d for viewing the cartridge 14. In one embodiment, the windows 110d are comprised of a transparent or translucent material. In one embodiment, the sleeve 110c includes three longitudinally spaced windows 110d. The windows 110d may extend around the sleeve 110c such that the cartridge 14 is visible on either side of one of the ribs 138.

Referring to FIGS. 2 and 2A, in use, the cap 26 of the cartridge 14 is inserted into the open proximal end 10b of the cartridge retainer 10 until the top surface 26a of the cap 26 contacts the one or more tabs 30. The cartridge 14 is further inserted into the cartridge retainer 10 causing the cap 26 to radially deflect the one or more tabs 30 out of the way. Before the bottom surface 26b of the cap 26 axially clears the one or more tabs 30, the top surface 26a of the cap 26 abuts the one or more deformable members 32. The cap 26 deforms the one or more deformable members 32 as the cartridge 26 is further inserted into the cartridge retainer 10 and the bottom surface 26b clears the one or more tabs 30 such that the one or more tabs 30 radially return to their initial position to abut the bottom surface 26b of the cap 26 and sandwich the cap 26 between the one or more deformable members 32 and the one or more tabs 30. The proximal end 10b of the cartridge retainer 10 may then be coupled to the housing 22 and the distal end 10a may be coupled to the hub 28 of the needle 16. The hub 28 may be detached from the distal end 10a of the cartridge retainer 10 and a new hub 28 and needle 16 may be attached to the distal end 10a of the cartridge retainer 10.

In one embodiment, the one or more deformable members 32 and the one or more tabs 30 render the cartridge 14 immobile relative to the cartridge retainer 10 at least under forces exerted to the components during use. In one embodiment, the one or more deformable members 32 and the one or more tabs 30 prevent the cartridge 14 from moving relative to the cartridge retainer 10 during attachment, detachment and reattachment of the needle 16 through the septum 24 such that no priming is required prior to injection even on the first dose.

In one embodiment, the one or more deformable members 32 and the one or more tabs 30 allow for dosages of less than approximately 0.100 mL to be administered to the patient using the injection device 10. In one embodiment, the one or more deformable members 32 and the one or more tabs 30 allow for dosages of less than approximately 0.090 mL to be administered to the patient using the injection device 10. In one embodiment, the one or more deformable members 32 and the one or more tabs 30 allow for dosages of less than approximately 0.080 mL to be administered to the patient using the injection device 10. In one embodiment, the one or more deformable members 32 and the one or more tabs 30 allow for dosages of less than approximately 0.070 mL to be administered to the patient using the injection device 10. In one embodiment, the one or more deformable members 32 and the one or more tabs 30 allow for dosages of less than approximately 0.060 mL to be administered to the patient using the injection device 10. In one embodiment, the one or more deformable members 32 and the one or more tabs 30 allow for dosages of less than approximately 0.050 mL to be administered to the patient using the injection device 10. In one embodiment, the one or more deformable members 32 and the one or more tabs 30 allow for dosages of less than approximately 0.040 mL to be administered to the patient using the injection device 10. In one embodiment, the one or more deformable members 32 and the one or more tabs 30 allow for dosages of less than approximately 0.030 mL to be administered to the patient using the injection device 10. In one embodiment, the one or more deformable members 32 and the one or more tabs 30 allow for dosages of less than approximately 0.020 mL to be administered to the patient using the injection device 10.

It will be appreciated by those skilled in the art that changes could be made to the exemplary embodiments shown and described above without departing from the broad inventive concepts thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and various features of the disclosed embodiments may be combined. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the methods of the present invention do not rely on the particular order of steps set forth herein, the particular order of the steps should not be construed as limitation on the claims. Any claims directed to the methods of the present invention should not be limited to the performance of their steps in the order written, and one skilled in the art can readily appreciate that the steps may be varied and still remain within the spirit and scope of the present invention.

We claim:

1. A cartridge retainer comprising:
   a sleeve having a distal end, a proximal end and a longitudinal axis extending between the distal end and the proximal end;
   one or more tabs extending radially from the sleeve toward the longitudinal axis and configured to engage a cartridge; and
   one or more deformable members extending axially from the distal end of the sleeve toward the one or more tabs and configured to deform in a longitudinal direction toward the distal end.

2. The cartridge retainer of claim 1, wherein the one or more deformable members include at least one projection.

3. The cartridge retainer of claim 2, wherein the at least one projection is a radially extending and axially projecting rib having a taper in the longitudinal direction.

4. The cartridge retainer of claim 2, wherein the at least one projection includes a plurality of projections spaced equally from one another around the longitudinal axis.

5. The cartridge retainer of claim 1, wherein the one or more deformable members is configured to deform such that a space between the one or more deformable members and the one or more tabs is variable.

6. The cartridge retainer of claim 1, wherein the one or more tabs are configured to radially deflect away from the longitudinal axis during insertion of a cap of a cartridge and at least partially return to an initial position to abut a bottom surface of the cap in an inserted position, and
   wherein the one or more deformable members are configured to abut a top surface of the cap and axially deform during insertion of the cartridge such that the cap is sandwiched between the one or more deformable members and the one or more tabs in the inserted position.

7. The cartridge retainer of claim 1, wherein the one or more tabs include a cantilever projection extending toward the distal end of the sleeve.

8. The cartridge retainer of claim 1, wherein the one or more tabs are substantially rigid in a longitudinal direction toward the proximal end of the sleeve.

9. The cartridge retainer of claim 1, wherein the one or more deformable members includes an elastomeric material.

10. The cartridge retainer of claim 9, wherein the one or more deformable members is an o-ring.

11. The cartridge retainer of claim 9, wherein the one or more deformable members is a spring.

12. The cartridge retainer of claim 1, wherein the one or more deformable members and the sleeve are comprised of the same material and are integrally formed.

13. The cartridge retainer of claim 1 further comprising a cartridge having a cap, wherein the cap is sandwiched between the one or more deformable members and the one or more tabs in an inserted position.

14. The cartridge retainer of claim 1, wherein the one or more tabs are configured to radially deflect away from the longitudinal axis.

15. A cartridge retainer comprising:
a sleeve having a distal end, a proximal end and a longitudinal axis extending between the distal end and the proximal end;
a plurality of cantilever tabs extending from an inner surface of the sleeve toward the distal end of the sleeve and the longitudinal axis and configured to radially deflect away from the longitudinal axis and configured to engage a cartridge; and
one or more projections integrally formed with the sleeve and extending axially from the distal end of the sleeve toward the one or more tabs and configured to deform in a longitudinal direction toward the distal end of the sleeve.

16. The cartridge retainer of claim 15, wherein the plurality of tabs are substantially rigid in a longitudinal direction toward the proximal end of the sleeve.

17. A cartridge retainer comprising:
a sleeve having a distal end, a proximal end and a longitudinal axis extending between the distal end and the proximal end; and
at least one contact member projecting radially inwardly from the sleeve toward the longitudinal axis, the at least one contact member configured to radially deform radially away from the longitudinal axis, the at least one contact member being configured to engage a cartridge.

18. The cartridge retainer of claim 17, wherein the at least one contact member includes at least three ribs that are each generally parallel with the longitudinal axis.

19. The cartridge retainer of claim 18, wherein the at least three ribs are coupled to one another by a ring comprised of an elastomeric material.

20. The cartridge retainer of claim 17, wherein the at least one contact member comprises an elastomeric material.

* * * * *